United States Patent
Poindexter et al.

[11] Patent Number: 6,054,590
[45] Date of Patent: Apr. 25, 2000

[54] IMIDAZOLONE ANORECTIC AGENTS: II. PHENYL DERIVATIVES

[75] Inventors: Graham S. Poindexter, Old Saybrook; Ildiko Antal, Cheshire, both of Conn.; Leah M. Giupponi, Basking Ridge, N.J.; Robert H. Stoffel, Hamden, Conn.; Kevin Gillman, Madison, Conn.; Mendi Higgins, Middletown, Conn.

[73] Assignee: Bristol-Myers Squibb Company, Princeton, N.J.

[21] Appl. No.: 09/261,670

[22] Filed: Mar. 3, 1999

Related U.S. Application Data

[60] Provisional application No. 60/079,359, Mar. 25, 1998.

[51] Int. Cl.$^7$ ............ C07D 233/32; C07D 233/48; A61K 31/4166; A61K 31/4164
[52] U.S. Cl. ............ 548/311.1; 514/58.5; 514/214; 514/235.8; 514/227.8; 514/255; 514/341; 514/359; 514/395; 514/397; 514/398; 544/139; 544/310; 546/210; 548/306.1; 548/311.7; 548/312.1; 548/314.7; 548/315.1; 548/315.4; 548/323.5; 548/324.1; 548/325.5; 540/520
[58] Field of Search ............ 548/325.5, 262.4, 548/311.1, 311.7, 312.1, 306.1, 314.7, 315.1, 315.4; 514/398, 58.5, 214, 235.8, 227.8, 255, 341, 359, 395, 397; 540/520; 544/139, 310; 546/210

[56] References Cited

U.S. PATENT DOCUMENTS 5,213,607  5/1993  Guaciaro .................. 504/193

FOREIGN PATENT DOCUMENTS 0735478  5/1943  Germany .................. 548/325.5
1258412  1/1968  Germany .................. 548/325.5

OTHER PUBLICATIONS

Gehlert et al., "Neuropeptide Y Receptor Antagonists in Obesity," *Expert Opinion on Investigational Drugs*, vol. 6, No. 12, Dec. 1997, pp. 1827–1838.

*Primary Examiner*—Floyd D. Higel
*Attorney, Agent, or Firm*—Richard P. Ryan

[57] ABSTRACT

A series of non-peptidergic antagonists of NPY have been synthesized and are comprised of phenyl derivatives of imidazolone compounds of Formula I.

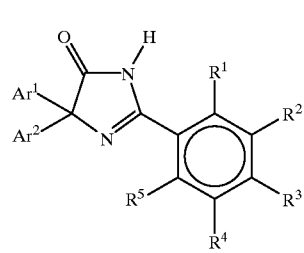

(I)

As antagonists of NPY-induced feeding behavior, these compounds and known analogs are expected to act as effective anorexiant agents in promoting weight loss and treating eating disorders.

9 Claims, No Drawings

IMIDAZOLONE ANORECTIC AGENTS: II. PHENYL DERIVATIVES

CROSS REFERENCE TO RELATED APPLICATION

This continuation-in-part application claims priority from provisional application U.S. Ser. No. 60/079,359 filed Mar. 25, 1998.

BACKGROUND OF THE INVENTION

The present invention concerns heterocyclic carbon compounds comprising 2-substituted phenyl derivatives of 5,5-diphenyl-3,5-dihydroimidazolones which have been discovered to be NPY antagonists.

2,5,5 (or 2,4,4)-triphenyl-2-imidazolin-4 (or 5)-ones, including analogs wherein the phenyl rings bear a para-alkyl, alkoxy, or halo substituent, have been described in the chemical literature, generally in connection with chemical process and organic chemical reaction mechanism studies.

Antagonism of neuropeptide Y receptors has been postulated to reduce food consumption in mammals. Several non-peptidic chemotypes have been disclosed in the literature as being antagonists at the $Y_1$ and at the $Y_5$ subtypes of NPY receptors. (See Gehlert and Hipskind, *Exp. Opin. Invest. Drugs,* 1997, 6, pp. 1827–1838.)

Neither applicants' novel 2-substituted phenyl derivatives of 5,5-diphenyl-dihydroimidazolones nor the use of these and related dihydroimidazolones for use in treating medical disorders by means of antagonizing NPY receptors following administration of these compounds is known or suggested by prior art.

SUMMARY AND DETAILED DESCRIPTION OF THE INVENTION

The present invention comprises compounds of Formula I, their

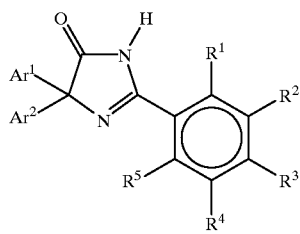

(I)

pharmaceutically acceptable acid addition salts and/or their hydrates thereof. In the foregoing structural Formula I, the symbols $R^1$ to $R^5$, $Ar^1$ and $Ar^2$ have the following meanings.

$R^1$ is hydrogen and halogen.

$R^2$ is hydrogen, halogen, $C_{1-6}$ alkyl, alkoxy, cyano, and trifluoromethyl.

$R^3$ is hydrogen, cyano, and trifluoromethyl.

$R^4$ is hydrogen, halogen, $C_{1-6}$ alkyl, formyl, carboxamido, cyano, nitro, trifluoromethyl, and $-(CH_2)_m-NR^6,R^7$; in which $R^6$ is hydrogen, $C_{1-6}$ alkyl, $C_{1-4}$ alkoxy-$C_{1-4}$ alkyl, $C_{2-6}$ alkenyl, $C_{1-6}$ alkoxy, $C_{3-8}$ cycloalkyl, $C_{1-4}$ carbalkoxy, and $CO_2H$; and $R^7$ is hydrogen, $C_{1-4}$ alkoxy-$C_{1-4}$ alkyl, Y-substituted $C_{1-6}$ alkyl, Y-substituted $C_{3-6}$ alkenyl,

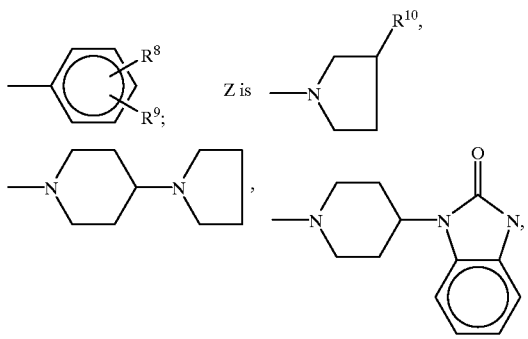

and $-(CH_2)_n-Z$.

$R^5$ is hydrogen, halogen, and $C_{1-6}$ alkoxy; with the proviso that $R^1-R^5$ cannot all be hydrogen simultaneously.

In the above structural variants:

$R^8$ is hydrogen, halogen, $C_{1-6}$ alkyl, alkoxy and nitro;

$R^9$ is hydrogen, halogen, $C_{1-6}$ alkyl, alkoxy, alkylcarbonyl, $C_{3-6}$ alkenyoxy, di $C_{1-4}$ alkylamino, di $C_{1-4}$ alkylamino-$C_{1-6}$ alkoxy, hydroxy, $-O_2C-C_{1-4}$ alkyl, phenoxy, and trifluoromethyl;

m and n are zero or 1;

Y is $C_{3-8}$ cycloalkyl, cyano, $CO_2H$, di $C_{1-4}$ alkylamino, hydroxy and

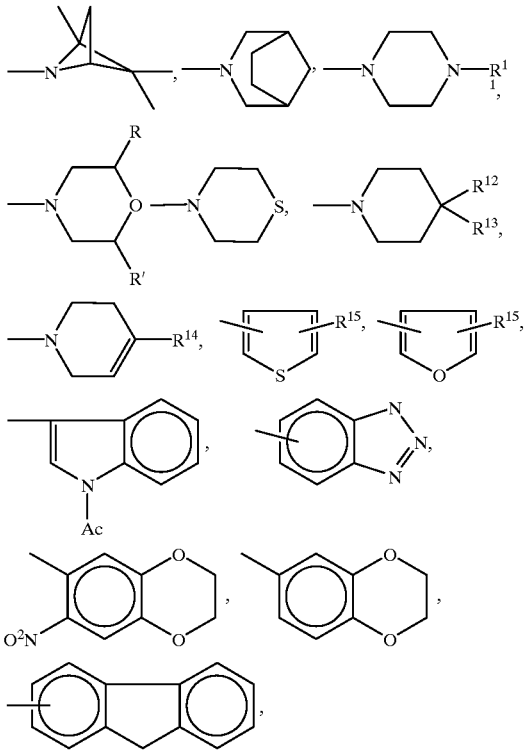

-continued

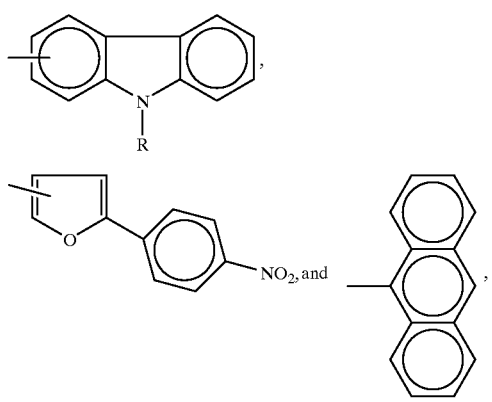

in which

R is hydrogen or $C_{1-4}$ alkyl;

$R^{10}$ is hydrogen, hydroxy, and $NCO_2R$;

$R^{11}$ is $C_{1-6}$ alkyl, $C_{3-8}$ cycloalkyl, $—CO_2R$, formyl, hydroxy-$C_{1-6}$alkyl, pyridine and $R^{16}$-substituted phenyl;

$R^{12}$ is hydrogen, $C_{1-6}$ alkyl, and cyano;

$R^{13}$ is hydrogen and phenyl;

$R^{14}$ is hydrogen and

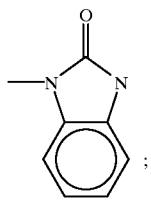

$R^{15}$ is hydrogen, halogen, and $C_{1-4}$ alkyl; and $R^{16}$ is $C_{1-4}$ alkoxy and nitro.

$Ar^1$ and $Ar^2$ are independently selected from

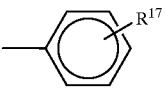

with $R^{17}$ being hydrogen, halogen, $C_{1-4}$ alkyl or alkoxy.

Preferred compounds are Formula I compounds wherein $Ar^1$ and $Ar^2$ are phenyl rings and $R^2$ is selected from halogen and nitro, with $R^1$ and $R^3$—$R^5$ being hydrogen.

Another aspect of the invention is the use of structurally related imidazolones to treat medical disorders involved with NPY receptor binding. In this regard, compounds of Formula II are to be administered for treatment of conditions and disorders in which binding at NPY receptors is implicated.

Formula II compounds have the following structural features.

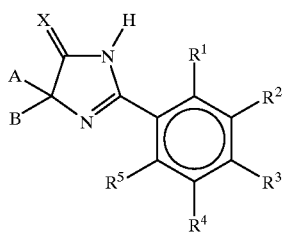

A and B are independently selected from phenyl, optimally substituted phenyl, indole, optimally substituted indole, thienyl, and furanyl. X is oxygen or sulfur. $R^1$—$R^5$ is as defined hereinabove except that $R^3$ can also be halogen and all of $R^1$—$R^5$ can be hydrogen simultaneously. As can be seen, Formula II is broader than and encompasses Formula I.

As indicated, the present invention also pertains to pharmaceutically acceptable salts of the Formula I and II compounds. Such salts include those derived from organic and inorganic acids such as, without limitation, hydrochloric, hydrobromic, phosphoric, sulfuric, methanesulfonic, acetic, fumaric, tartaric, moleic, succinic, lactic, citric acid, and the like.

Formula I compounds can be produced by using the processes shown in Scheme 1. The symbols $Ar^1$, $Ar^2$ and $R^1$—$R^5$ are as previously defined.

Scheme 1

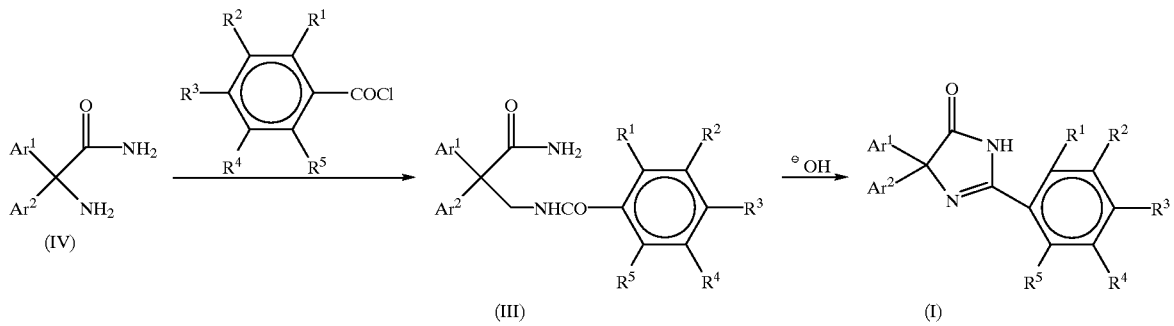

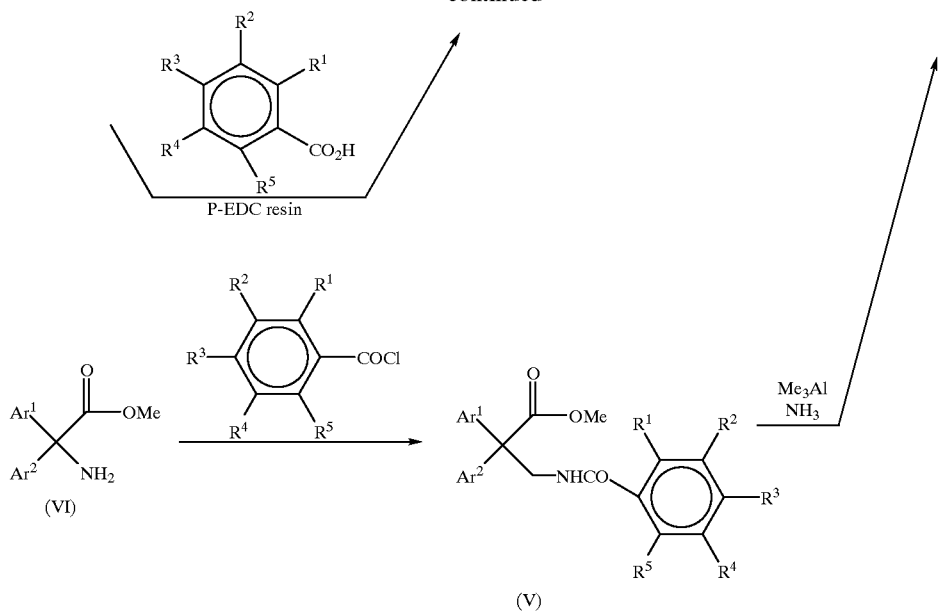

Unless otherwise indicated in the Specific Embodiments section, known intermediates IV and VI were prepared by standard literature methods. (A typical synthesis of Formula IV compounds is described by Edward, et al., *Can. J. Chem.,* 1967, 45, p. 1925. A typical Formula VI compound synthesis is described by Skelly, et al., *J. Org. Chem.,* 1985, 50, p. 267).

Using various Formula I compounds as synthetic intermediates, other phenyl derivatives can be elaborated providing additional examples of Formula I compound structures. Synthetic Schemes 2–8 illustrate many of these conversions of simple to more complex Formula I products. These schemes, while showing specific compound examples, are general in nature and are adaptable by one skilled in organic synthesis to provide other Formula I products.

Scheme 2

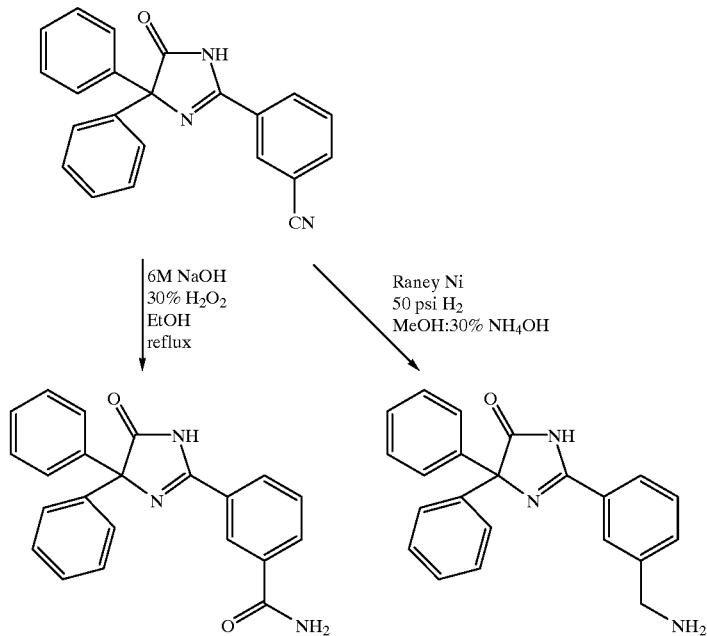

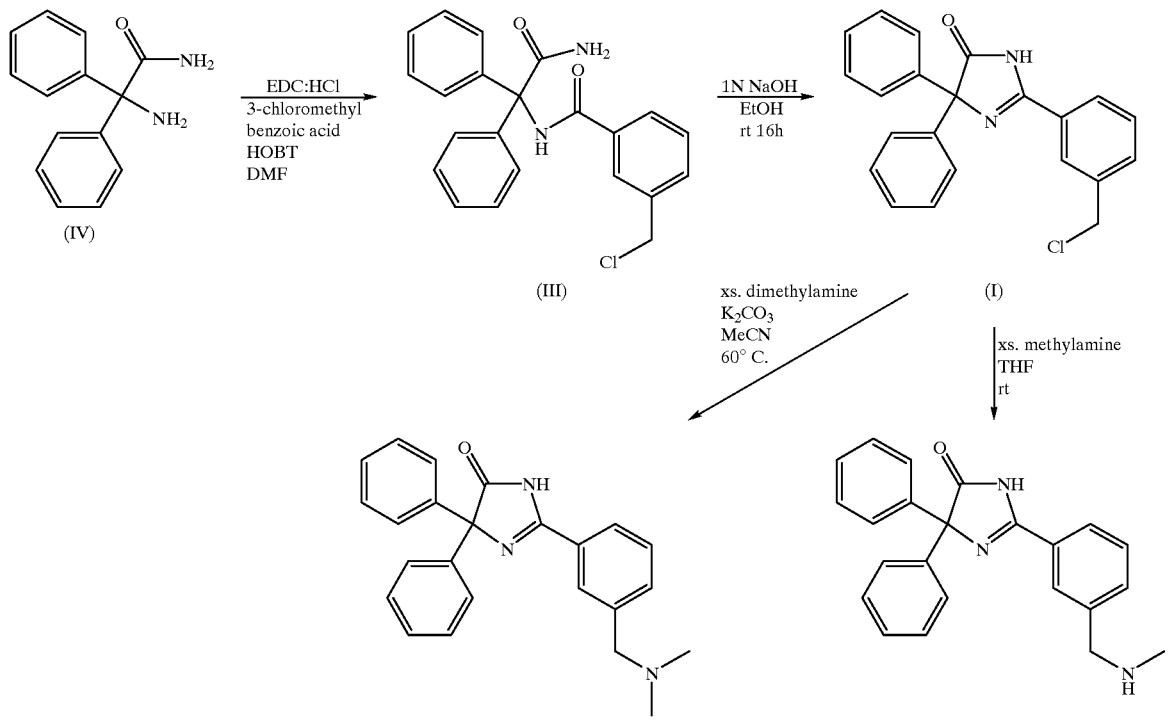
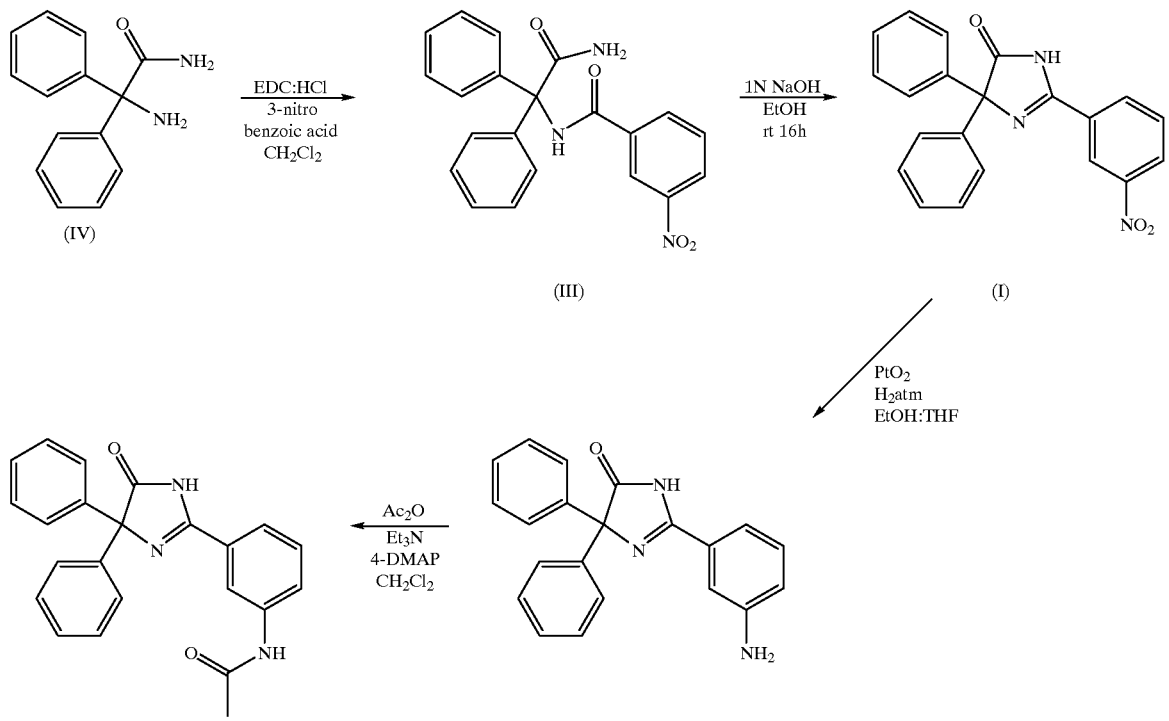

Scheme 5
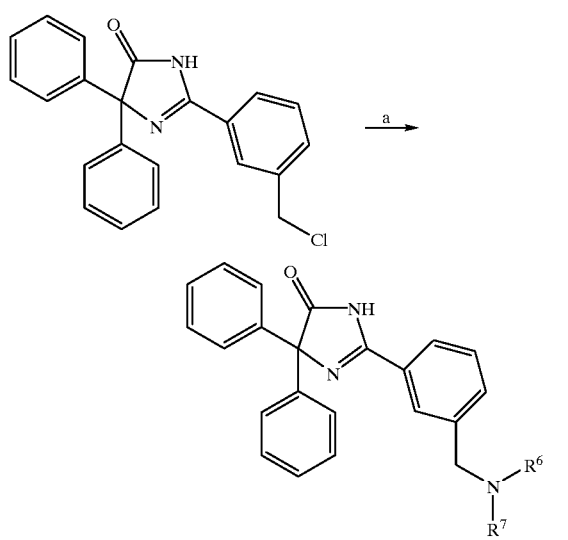
(a) R⁶R⁷NH, K₂CO₃ (2° only), CH₃CN, 60° C.
(a) Y—CHO/Z—CHO, NaBH(OAc)₃, AcOH, 1,2-dichloroethane, overnight (b) same as (a) except 5.0 eq. AcOH, 4 days.
Scheme 7
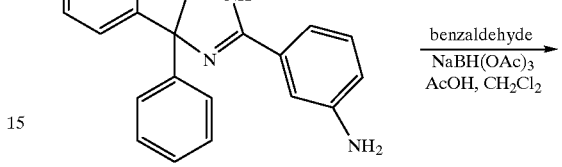
Scheme 6
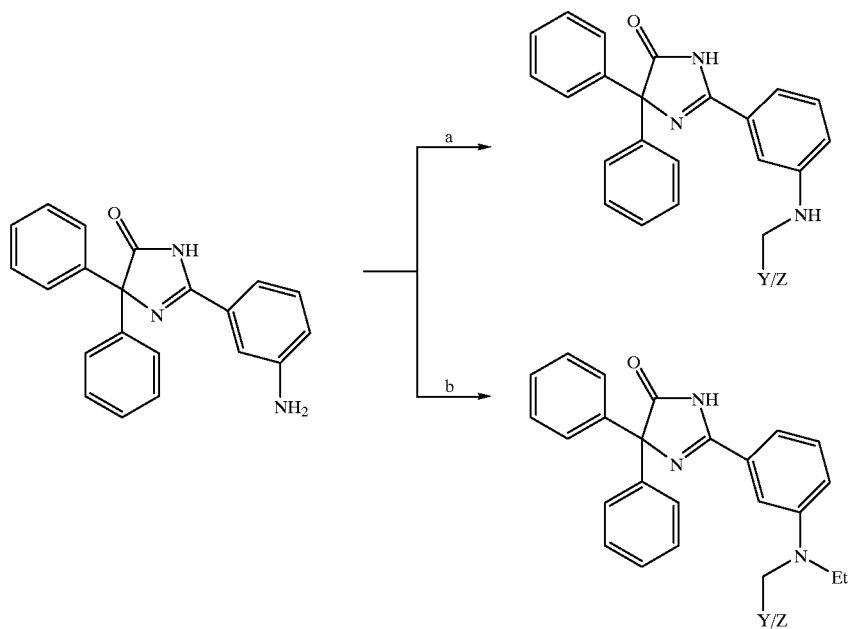

-continued

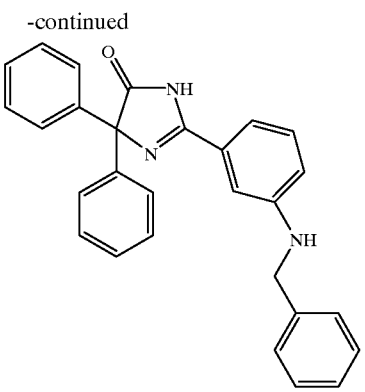

Scheme 8

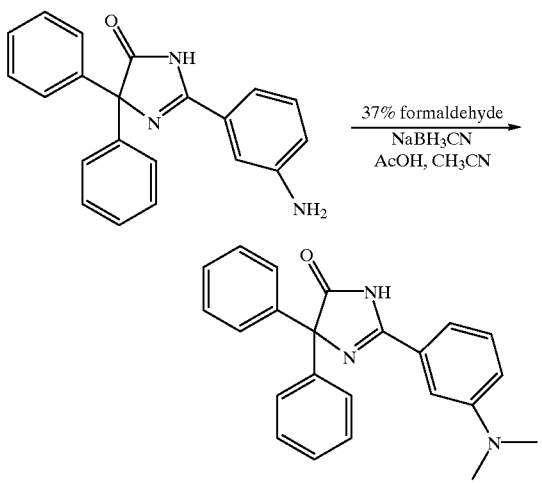

Additional specific examples of these synthetic transformations will be given in the Specific Embodiments section and will provide additional experimental detail.

Similar processes, such as Schemes 1–8, employing appropriate modifications can be utilized to provide compounds of Formula II. In addition, synthesis of certain Formula II compounds can be found in the chemical literature. Various reaction intermediates and Formula II products can be prepared by modifications known to one skilled in the art. Additional examples and procedures are provided infra.

The compounds of Formulas I and II demonstrate binding affinity at NPY receptors. The binding interaction has been characterized as antagonism at NPY $Y_5$ receptors. This pharmacologic activity was characterized by using BRI-TN-5BI-4 insect cells infected with NPY $Y_5$-recombinant Baculovirus. These cells which express $Y_5$ receptor were used in a radioligand binding assay employing Iodine-125 labeled PYY ligand. The imidazolones of this invention all showed $IC_{50}$ values of less than 1 $\mu$M.

Formula I and II compounds have good binding affinities as evidenced by $IC_{50}$ values being about 10 $\mu$M or less at NPY $Y_5$ receptors. Preferred compounds have $IC_{50}$ values less than 200 nM.

Pharmacologically, these compounds act as selective NPY antagonists at NPY $Y_5$ receptor sites. As such, the compounds of Formulas I and II are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or II or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:
  disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;
  conditions related to increased sympathetic nerve activity for example, during or after coronary artery surgery, and operations and surgery in the gastrointestinal tract;
  cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;
  conditions related to pain or nociception;
  diseases related to abnormal gastrointestinal motility and secretion, such as different forms of ileus, urinary incontinence, and Crohn's disease;
  abnormal drink and food intake disorders, such as obesity, anorexia, bulimia, and metabolic disorders;
  diseases related to sexual dysfunction and reproductive disorders;
  conditions or disorders associated with inflammation;
  respiratory diseases, such as asthma and conditions related to asthma and bronchoconstriction;
  diseases related to abnormal hormone release, such as leutinizing hormone, growth hormone, insulin and prolactin;
  sleep disturbance and diabetes.

There is evidence that NPY contributes to certain symptoms in these disorders: hypertension, eating disorders, and depression/anxiety; as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a compound of Formula I or II or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anorectic effects without causing any harmful or untoward side effects. Similarly, the instant compounds can be administered to treat the various diseases, conditions, and disorders listed supra.

Therapeutically, the instant compounds are generally given as pharmaceutical compositions comprised of an effective anorectic amount of a compound of Formula I or II or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyetheleneglycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were generally employed using potassium bromide (KBr) as diluent. The elemental analyses are reported as percent by weight. Melting points were obtained using a Thomas Hoover capillary apparatus and are uncorrected. Mass spectra (m/z; MH$^+$) and analytic HPLC (retention time and peak area %) data were obtained.

EXAMPLE 1

General Acylation/Cyclization Procedure for the Preparation of Imidazolones

α-Amino-α,α-diarylacetamide (IV) (0.050 g, 0.22 mmol) was added to a solution of the corresponding carboxylic acid (0.44 mmol), and 0.690 g of P-EDC resin (1.4 meq/g, 0.88 mmol) in 5 ml dry CH$_2$Cl$_2$. [P-EDC resin was synthesized as described by known literature procedures (e.g., Desai, et al., *Tetrahedron Lett.*, 1993, 48, p. 7685) and is as follows: To a stirred solution of 1-[3-(dimethylamino)propyl]-3-ethylcarbodiimide (13.02 g, 84 mmole) in 50 mL anhydrous N,N-dimethylformamide (DMF) was added chloromethylated polystyrene-divinylbenzene 2% resin (50 g, 70 meq. of Cl; 200–400 mesh, 1.4 meq. Cl/g). After stirring at 100° C. overnight, the mixture was cooled and filtered. The resin was washed (200 mL×3) each with DMF, tetrahydrofuran (THF), and diethyl ether. The resin was then dried in vacuo under reduced pressure providing 60.8 g of P-EDC.]

The reaction mixture was shaken for 36 h at rt, then the crude reaction mixture was filtered and the filter cake was washed with excess CH$_2$Cl$_2$. The resulting filtrate was evaporated in vacuo to yield a crude solid. This solid was dissolved in 3 mL EtOH and 0.5 mL of 1N NaOH(aq.). The resulting solution was stirred for 16 h then neutralized with 1N HCl(aq). The solvent was evaporated in vacuo and the crude solid was purified by reverse phase HPLC chromatography (YMC Inc., 20×100 mm, 5 µm particle size, 120 Å pore size, C18 stationary phase, ODS-A fast elution: 50–100% (10%MeOH/90%H$_2$O-0.1%TFA):(90%MeOH/10%H$_2$O-0.1%TFA) providing pure imidazolones of Formulas I and II.

Using this procedure with reactants being α-amino-α,α-diphenylacetamide and 3-cyanobenzoic acid gave product in Example 2.

EXAMPLE 2

2-(3-Cyanophenyl)-3,5-dihydro-5,5-diphenyl-4H-imidazol-4-one

This compound was isolated as an off white solid in 5% yield. White solid (mp 236–237° C.); $^1$H-NMR (CDCl$_3$, 300 MHz) δ=10.85 (brs, 1H), 8.43 (s, 1H), 8.24 (d, 1H, J=6.0 Hz), 7.84 (d, 2H, J=6.0 Hz), 7.61 (t, 1H, J=6.0 Hz), 7.58 (d, 4H, J=6.0 Hz), 7.35 (m, 6H); LRMS m/z (ESI) 338.36 (M+H)$^+$; IR (KBr): cm$^{-1}$ 3067, 2231, 1713, 1634, 1605, 1174, 696; HPLC ret time 7.38 min; Anal. Calcd for C$_{22}$H$_{15}$N$_3$O: C, 78.32; H, 4.48; N, 12.45. Found: C, 78.51; H, 4.46; N, 12.33.

EXAMPLE 3

2,5,5-Triphenyl-3,5-dihydro-imidazol-4-one

This Formula II compound was prepared by standard procedure as referenced in the literature (Cf: Rio, et al., *Bull. Soc. Chim. Fr.*, 1958, 98, p. 543). All spectroscopic data was consistent with the assigned structure. White solid (mp 238–239° C.); $^1$H-NMR (CDCl$_3$, 300 MHz) δ=7.98 (d, 2H, J=6.0 Hz), 7.51 (d, 4H, J=6.0 Hz), 7.41 (m, 3H), 7.26 (m, 6H); LRMS m/z (ESI) 311 (M−H)$^-$; Anal. Calcd for C$_{21}$H$_{16}$N$_2$O: C, 80.748; H, 5.163; N, 8.968. Found: C, 80.47; H, 5.06; N, 8.94.

Utilization of Scheme 1 processes will produce the following products.

EXAMPLE 4

2-[4-(Trifluoromethyl)phenyl]-3,5-dihydro-5,5-diphenyl-4H-imidazol-4-one

This compound was isolated as an off white solid in 5% yield. LRMS m/z (ESI) 381.06 (M+H)$^+$; HPLC ret time 8.95 min.

EXAMPLE 5

2-(2,5-Dimethoxyphenyl)-3,5-dihydro-5,5-diphenyl-4H-imidazol-4-one

This compound was isolated as an off white solid in 2% yield. LRMS m/z (ESI) 373.09 (M+H)$^+$; HPLC ret time 7.63 min.

EXAMPLE 6

2-(2,3,5,6-Tetrafluorophenyl)-3,5-dihydro-5,5-diphenyl-4H-imidazol-4-one

This compound was isolated as an off white solid in 16% yield. LRMS m/z (ESI) 385.04 (M+H)+; HPLC ret time 7.67 min.

EXAMPLE 7

2-(3-Bromophenyl)-3,5-dihydro-5,5-diphenyl-4H-imidazol-4-one

This compound was isolated as an off white solid in 15% yield. LRMS m/z (ESI) 391.16 (M+H)$^+$; HPLC ret time 4.10 min.

EXAMPLE 8

2-(3-Fluorophenyl)-3,5-dihydro-5,5-diphenyl-4H-imidazol-4-one

This compound was isolated as an off white solid in 21% yield. LRMS m/z (ESI) 331.24 (M+H)$^+$; HPLC ret time 3.80 min.

EXAMPLE 9

2-(3-Chlorophenyl)-3,5-dihydro-5,5-diphenyl-4H-imidazol-4-one

This compound was isolated as an off white solid in 16% yield. LRMS m/z (ESI) 347.19 (M+H)$^+$; HPLC ret time 4.03 min.

EXAMPLE 10

2-(3-Iodophenyl)-3,5-dihydro-5,5-diphenyl-4H-imidazol-4-one

This compound was isolated as an off white solid in 16% yield. LRMS m/z (ESI) 439.19 (M+H)$^+$; HPLC ret time 4.14 min.

EXAMPLE 11

2-(3-Trifluoromethylphenyl)-3,5-dihydro-5,5-diphenyl-4H-imidazol-4-one

This compound was isolated as an off white solid in 22% yield. LRMS m/z (ESI) 381.23 (M+H)$^+$; HPLC ret time 4.13 min.

EXAMPLE 12

2-(3-Methylphenyl)-3,5-dihydro-5,5-diphenyl-4H-imidazol-4-one

This compound was isolated as an off white solid in 5% yield. LRMS m/z (ESI) 327.27 (M+H)$^+$; HPLC ret time 3.67 min.

EXAMPLE 13

2-(3,5-Dimethylphenyl)-3,5-dihydro-5,5-diphenyl-4H-imidazol-4-one

This compound was isolated as an off white solid in 2% yield. LRMS m/z (ESI) 341.27 (M+H)$^+$; HPLC ret time 3.66 min.

EXAMPLE 14

2-(4-Cyanophenyl)-3,5-dihydro-5,5-diphenyl-4H-imidazol-4-one

This compound was isolated as an off white solid in 14% yield. LRMS m/z (ESI) 338.24 (M+H)$^+$; HPLC ret time 3.70 min.

EXAMPLE 15

2-(4-Fluorophenyl)-3,5-dihydro-5,5-diphenyl-4H-imidazol-4-one

This compound was isolated as an off white solid in 4% yield. LRMS m/z (ESI) 331.24 (M+H)$^+$; HPLC ret time 3.65 min.

EXAMPLE 16

2-(3-Formylphenyl)-3,5-dihydro-5,5-diphenyl-4H-imidazol-4-one

This compound was isolated as an off white solid in 18% yield. LRMS m/z (ESI) 341.22 (M+H)$^+$; HPLC ret time 3.61 min.

The following examples are prepared in accordance with the syntheses of Scheme 2.

EXAMPLE 17

2-(3-Aminomethylphenyl)-3,5-dihydro-5,5-diphenyl-4H-imidazol-4-one

To a glass bomb was added 100 mg (0.296 mmol) of the compound of Example 2, the 3-cyanophenyl derivative, and 10 mg of freshly washed Raney nickel in 6 mL of a 5:1 MeOH:NH$_4$OH(conc.) solution. The reaction vessel was charged with 50 psi hydrogen and shaken overnight. Upon completion the reaction was filtered through Celite and the solvent was evaporated in vacuo. Chromatography of the crude solid (Silica gel/Hexanes:Acetone 2:1) produced 65 mg (64%) of the desired amine as an off-white solid. LRMS m/z (ESI) 342.3 (M+H).

EXAMPLE 18

2-(3-Aminocarbonylphenyl)-3,5-dihydro-5,5-diphenyl-4H-imidazol-4-one

To a 50 mL flask was added 0.300 g (0.889 mmol) of the 3-cyano derivative (Example 2) and 6 mL of 95% EtOH. The solution was stirred until homogeneous and then 1 mL of 6M NaOH and 1 mL of 30% hydrogen peroxide were added and the rxn was heated to reflux and allowed to stir for 3 h. Upon completion the reaction was cooled to rt and neutralized with conc. HCl. The solvent was evaporated in vacuo, and the crude residue was purified by column chromatography (Silica gel/Hexanes:Acetone 4:1) producing 0.20 g (63%) of the desired amide as a white solid. LRMS m/z (ESI) 356.2 (M+H)$^+$; $^1$H-NMR (DMSO-d$_6$, 300MHz) δ=8.74 (s, 1H), 8.32 (d, 1H, J=6.0 Hz), 8.10 (d, 1H, J=6.0 Hz), 7.66 (t, 1H, J=6.0 Hz), 7.48 (d, 4H, J=6.0 Hz), 7.33 (m, 6H).

The following examples are prepared in accordance with the syntheses of Scheme 3.

EXAMPLE 19

2-(3-Chloromethylphenyl)-3,5-dihydro-5,5-diphenyl-4H-imidazol-4-one

To a 100 mL flask was added 1.0 g (4.42 mmol) of amine (IV), 0.830 g (4.87 mmol) of 3-chloromethylbenzoic acid, and 0.658 g (4.87 g) of 1-hydroxybenzotriazole. The solids were dissolved in 20 mL dry DMF and the reaction was stirred until homogeneous then cooled to 0° C. EDC:HCl (4.87 mmol) was added in one portion and the reaction was allowed to warm slowly to rt and stirred overnight. Upon completion the solvent was evaporated in vacuo and the oil was dissolved in dichloromethane and washed with 1N HCl. The organic layer was then separated, dried (Na$_2$SO$_4$) and evaporated in vacuo to yield a crude solid. Chromatography of the crude solid (Silica gel/Hexanes:Acetone 4:1) produced 0.520 g (31%) of the desired amide (III) as a white solid. Treatment of amide (III) with 2.0 mL of 1N NaOH in 10 mL ethanol for 1 h followed by neutralization with 1N HCl and evaporation of the solvent produced the desired benzylchloride product which was purified by column chromatography (Silica gel/Hexanes:Acetone 4:1) affording 0.250 g (51%) of the desired product as a white solid.

EXAMPLE 20

2-(3-Dimethylaminomethylphenyl)-3,5-dihydro-5,5-diphenyl-4H-imidazol-4-one

Reacting the benzyl chloride product (Example 19) (0.227 mmol) in a sealed tube with xs. dimethylamine, (0.55 mmol) anhydrous potassium carbonate in 3 mL dry acetonitrile at 60° C. overnight followed by evaporation of the solvent in vacuo produced the desired benzyldimethylaminoimidazolone product. Purification of the crude solid by chromatography (Silica gel/Hexanes:Acetone 2:1) afforded 0.100 g (98%) of product as a white solid. LRMS m/z (ESI) 370.3 (M+H)$^+$; $^1$H-NMR (CDCl$_3$, 300 MHz) δ=8.52 (s, 1H), 8.34 (d, 1H, J=6.0 Hz), 7.71 (d, 1H, J=6.0 Hz), 7.51 (t, 1H, J=6.0 Hz), 7.43 (m, 4H), 7.28 (m, 6H), 4.22 (s, 2H), 2.75 (s, 6H).

EXAMPLE 21

2-(3-Methylaminomethylphenyl)-3,5-dihydro-5,5-diphenyl-4H-imidazol-4-one

To a glass bomb was added benzyl chloride product (Example 19) 0.107 g (0.297 mmol) and excess anhydrous methylamine (4.0 mL of a 2.0M solution in THF). The reaction vessel was sealed and stirred at rt overnight. Upon completion the solvent was evaporated in vacuo producing an off white solid. Purification of the crude solid (C$_{18}$ stationary phase ODS-A fast elution: 50–100% (10%MeOH/90%H$_2$O-0.1%TFA):(90%MeOH/10%H$_2$O-0.1%TFA)) produced 0.070 g (67%) of the desired amine as a white solid. LRMS m/z (ESI) 356.2 (M+H)$^+$; $^1$H-NMR (MeOH-d$_4$, 300 MHz) δ=8.26 (s, 1H), 8.10 (d, 1H, J=6.0 Hz), 7.79 (d, 1H, J=6.0 Hz), 7.71 (t, 1H, J=6.0 Hz), 7.49 (d, 4H, J=6.0 Hz), 7.32 (m, 6H), 4.31 (s, 2H), 2.77 (s, 3H).

The following examples are prepared in accordance with the syntheses of Scheme 4.

EXAMPLE 22

2-(3-Nitrophenyl)-3,5-dihydro-5,5-diphenyl-4H-imidazol-4-one

To a 250 mL flask was added 1.0 g (4.42 mmol) of amine (IV), and 1.11 g (6.64 mmol) of 3-nitrobenzoic acid. The solids were dissolved in 40 mL dry CH$_2$Cl$_2$ and the reaction was stirred until homogeneous then cooled to 0° C. EDC:HCl (7.07 mmol) was added in one portion and the reaction was allowed to warm slowly to rt and stirred overnight. Upon completion the organic layer was washed with 0.5N HCl. The organic layer was then separated, dried (Na$_2$SO$_4$) and evaporated in vacuo to yield a crude solid. The crude amide (III), 1.13 g (68%) was carried onto the next step unpurified. Treatment of amide (III) with 4.0 mL of 1N NaOH in 20 mL ethanol for 16 h followed by netralization with 1N HCl and evaporation of the solvent produced the desired 3-nitrobenzylimidazolone, which was purified by column chromatography (Silica gel/Hexanes:Acetone 3:1) affording 0.744 g (69%) of the desired imidazolone product as a light yellow solid. LRMS m/z (ESI) 358.3 (M+H)$^+$; $^1$H-NMR (DMSO-d$_6$, 300 MHz) δ=12.17 (brs,1H), 8.93 (s, 1H), 8.52 (d, 1H, J=6.0 Hz), 8.47 (d, 1H, J=6.0 Hz), 7.88 (t, 1H, J=6.0 Hz), 7.48 (m, 4H), 7.35 (m, 6H); Anal. Calcd for C$_{21}$H$_{15}$N$_3$O$_3$: C, 70.58; H, 4.23; N, 11.76. Found: C, 70.29; H, 4.39; N, 11.49.

EXAMPLE 23

2-(3-Aminophenyl)-3,5-dihydro-5,5-diphenyl-4H-imidazol-4-one

To a 100 mL flask was added 0.614 g (1.72 mmol) of the 3-nitrophenyl product (Example 22) and 0.092 g of platinum (IV) oxide in 20 mL of a 8:1 EtOH:THF solution. The reaction vessel was charged with 5 psi hydrogen and stirred overnight. Upon completion the reaction was filtered through Celite and the solvent was evaporated in vacuo. Chromatography of the crude solid (Silica gel/Hexanes:Acetone 4:1) produced 0.480 g (85%) of the desired amine product as a white solid. LRMS m/z (ESI) 328.3 (M+H)$^+$; $^1$H-NMR (CDCl$_3$, 300 MHz) δ=7.60 (d, 4H, J=6.0 Hz), 7.41 (s, 1H), 7.35 (m, 6H), 7.19 (m, 1H), 6.85 (m, 1H), 6.41 (d,1 H, J=6.0 Hz).

EXAMPLE 24

2-(3-Acetamidophenyl)-3,5-dihydro-5,5-diphenyl-4H-imidazol-4-one

To a 25 mL round bottom flask was added 0.103 g (0.315 mmol) of the 3-aminophenyl product (Example 23), acetic anhydride (0.63 mmol), triethylamine (0.787 mmol) and 4-dimethylaminopyridine 0.010 g in 3 mL dry dichloromethane. The reaction was stirred at rt overnight, and upon completion was quenched with 10% aqueous sodium carbonate. The organic layer was separated, dried (Na$_2$SO$_4$) and evaporated in vacuo. The crude oil was purified by column chromatography (C$_{18}$ stationary phase ODS-A fast elution: 50–100% [(10%MeOH/90%H$_2$O-0.1%TFA):(90%MeOH/10%H$_2$O-0.1%TFA)] producing 0.060 g (40%) of the desired acetamide product as a white solid. LRMS m/z (ESI) 368.3 (M–H)$^+$; $^1$H-NMR (CDCl$_3$, 300 MHz) δ=8.36 (s, 1H), 7.79 (m, 2H), 7.38 (m, 4H), 7.29 (m, 6H), 7.06 (t, 1H, J=6.0 Hz), 2.02 (s, 3H).

The following aminomethylphenyl derivatives were synthesized in accordance with Scheme 5.

TABLE 1

| Example No. | R$^6$ | R$^7$ | Yield (%) |
|---|---|---|---|
| 25 | H | (CH$_2$)$_3$NPr$_2$ | 9 |
| 26 | H | —CH(CH$_3$)Ph | 10 |
| 27 | H | —CH(i-Pr)CH$_2$OH | 9 |
| 28 | H | 2,4-diClbenzyl | 49 |
| 29 | H | 2-benzodioxole | 56 |
| 30 | H | 4-MePh | 11 |
| 31 | H | Ph | 11 |
| 32 | H | 4-Fph | 13 |
| 33 | H | 2-benzotriazole | 21 |
| 34 | H | 4-NO$_2$Ph | 9 |
| 35 | Pr | cyclopropyl | 76 |
| 36 | Me | —CH$_2$CH$_2$OH | 39 |
| 37 | Me | c-hexyl | 100 |
| 38 | Me | —C(Me)$_2$CO$_2$H | 44 |
| 39 | | cyclopentyl-OH | 53 |
| 40 | | 1-cyclohexyl-benzimidazol-2(3H)-one | 47 |
| 41 | | piperidine-N-CHO | 64 |

TABLE 1-continued
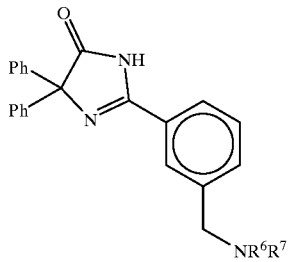
| Example No. | R⁶ | R⁷ | Yield (%) |
|---|---|---|---|
| 42 | | 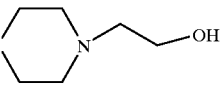 | 85 |
| 43 | |  | 71 |
| 44 | | 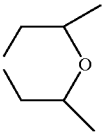 | 100 |
| 45 | | 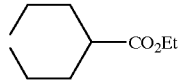 | 83 |
| 46 | | 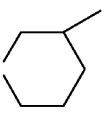 | 100 |
| 47 | Me | CH₂Ph | 100 |
| 48 | Me | n-Bu | 100 |
| 49 | | 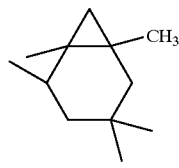 | 100 |
| 50 | Me | C₂(Me)CO₂H | 13 |
| 51 | | 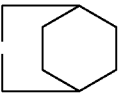 | 60 |
| 52 | Me | (CH₂)₂NMe₂ | 93 |
| 53 | | 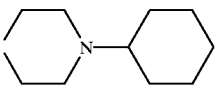 | 71 |
| 54 | Me | 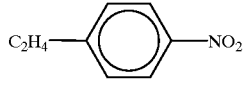 | 80 |
| 55 | (CH₂)₂OMe | (CH₂)₂OMe | 90 |

TABLE 1-continued
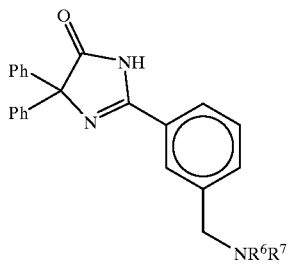
| Example No. | R⁶ | R⁷ | Yield (%) |
|---|---|---|---|
| 56 | | 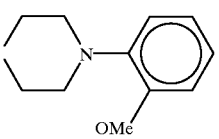 | 43 |
| 57 | |  | 96 |
| 58 | Me | CH(Me)Ph | 27 |
| 59 | | 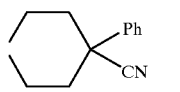 | 76 |
| 60 | Me | —CH₂CN | 30 |
| 61 | C-Hex | (CH₂)₂CO₂H | 49 |
| 62 | | 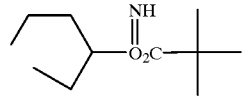 | 45 |
| 63 | | 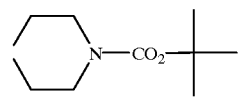 | 59 |
| 64 | |  | 100 |
| 65 | | 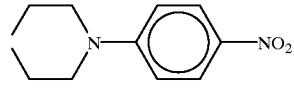 | 6 |
| 66 | | 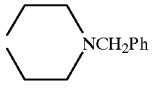 | 25 |
| 67 | H | —CH(CO₂H)CH₂——NO₂ | 6 |
| 68 | | 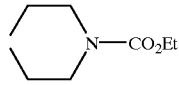 | 64 |

TABLE 1-continued
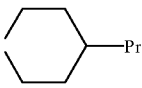
| Example No. | R[6] | R[7] | Yield (%) |
|---|---|---|---|
| 69 | |  | 36 |
| 70 | | 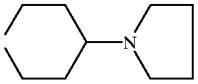 | 42 |
| 71 | | 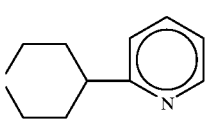 | 18 |
| 72 | | 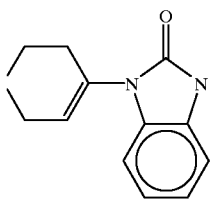 | 38 |
| 73 | | 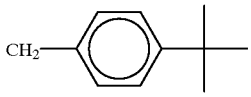 | 12 |
Similar examples of Formula I compounds made via the syntheses shown in Scheme 6 are displayed below in Table 2.
TABLE 2
| Example No. | R[6] | R[7] | Yield (%) |
|---|---|---|---|
| 74 | H | 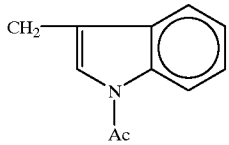 | 70 |
| 75 | H | 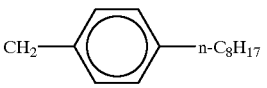 | 13 |
| 76 | H | 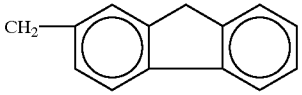 | 9 |
| 77 | H | 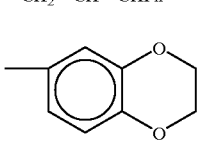 | 24 |
| 78 | H | $CH_2$—CH=CHPh | 38 |
| 79 | H | 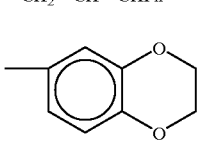 | 12 |

TABLE 2-continued

| Example No. | R⁶ | R⁷ | Yield (%) |
|---|---|---|---|
| 80 | H | —CH₂—C₆H₄—OEt (2-EtO) | 100 |
| 81 | H | —CH₂—CMe=CHMe | 70 |
| 82 | H | —CH₂—C₆H₄—OC₅H₁₁ (4-) | 71 |
| 83 | H | —CH₂—(3-Me-thiophen-2-yl) | 55 |
| 84 | H | —CH₂—C₆H₄—OMe (3-) | 44 |
| 85 | H | —CH₂—C₆H₄—O—C₆H₄—Me (4-,4'-) | 44 |
| 86 | H | —CH₂—C₆H₃(Me)₂ (3,4-di-Me) | 64 |
| 87 | H | —CH₂—C₆H₃(OH)(NO₂) (3-OH, 4-NO₂) | 6 |
| 88 | H | —CH₂—C₆H₄—OCH₂—CH=CH₂ (4-) | 77 |
| 89 | H | —CH₂—(4-Br-thiophen-2-yl) | 75 |
| 90 | H | —CH₂—C₆H₃(F)(CF₃) (3-F, 4-CF₃) | 70 |
| 91 | H | —CH₂—C₆H₄—Br (4-) | 75 |
| 92 | H | —CH₂—C₆H₄—O(CH₂)₂NMe₂ (4-) | 22 |
| 93 | H | —CH₂—(furan-2-yl)-C₆H₄—NO₂ (5-(4-NO₂-phenyl)furan-2-yl) | 10 |
| 94 | H | —CH₂—C₆H₄—NO₂ (3-) | 4 |
| 95 | H | —CH₂—(9-Et-carbazol-3-yl) | 45 |
| 96 | H | —CH₂—C₆H₄—CF₃ (3-) | 56 |
| 97 | H | —CH₂—C₆H₃(OMe)₂ (3,4-di-OMe) | 19 |
| 98 | H | —CH₂—(anthracen-9-yl) | 31 |
| 99 | H | —CH₂—C₆H₃(NO₂)(Cl) (3-NO₂, 4-Cl) | 65 |
| 100 | H | —CH₂—(6-NO₂-benzo[1,3]dioxol-5-yl) | 15 |
| 101 | H | —CH₂—(furan-2-yl) | 50 |
| 102 | H | —CH₂—C₆H₄—F (4-) | 46 |

TABLE 2-continued

| Example No. | R⁶ | R⁷ | Yield (%) |
|---|---|---|---|
| 103 | H | 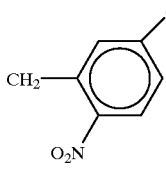 4-Cl, 2-O₂N-benzyl | 28 |
| 104 | Et | 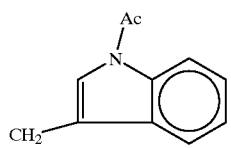 N-Ac-indol-3-ylmethyl | 4 |
| 105 | Et | 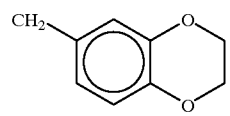 2,3-dihydrobenzo[1,4]dioxin-6-ylmethyl | 23 |
| 106 | Et | 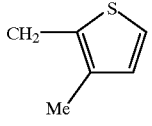 3-methylthiophen-2-ylmethyl | 54 |
| 107 | Et | 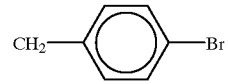 4-bromobenzyl | 46 |
| 108 | Et | 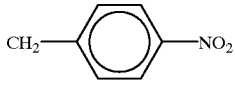 4-nitrobenzyl | 44 |
| 109 | Et | 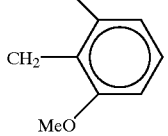 2,6-dimethoxybenzyl | 9 |
| 110 | Et | 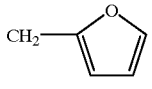 furan-2-ylmethyl | 16 |
| 111 | Et | 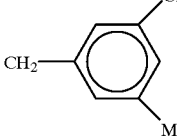 3-chloro-5-methylbenzyl | 23 |

EXAMPLE 112

Receptor Binding Assay

Human cDNA of the NPY Y₅ receptor was PCR-corrected in Baculovirus which was then used to infect "Hi5" (BTI-TN-5BI-4) insect cells during 48 hr incubation. The cells were harvested and used for the binding assay using iodine-125-labeled-PYY ([$^{125}$I]PYY) as a radioligand. Saturation binding used 0.05–100 nM [$^{125}$I]PYY. Nonspecific binding was determined in the presence of 1000 nM unlabeled PYY and was less than 20% of total binding.

What is claimed is:

1. A compound of Formula I or its pharmaceutically acceptable

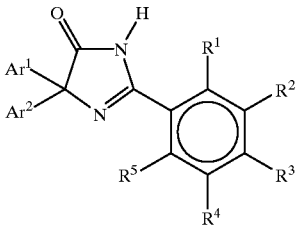

(I)

acid addition salts or hydrates thereof, wherein $R^1$ is hydrogen or halogen;

$R^2$ is hydrogen, halogen, $C_{1-6}$ alkyl, alkoxy, cyano, or trifluoromethyl;

$R^3$ is hydrogen, cyano, or trifluoromethyl;

$R^4$ is hydrogen, halogen, $C_{1-6}$ alkyl, formyl, carboxamido, cyano, nitro, or —(CH₂)ₘ—NR⁶,R⁷;

$R^5$ is hydrogen, halogen, $C_{1-6}$ alkoxy; with the proviso that $R^1$—$R^5$ cannot all be hydrogen at the same time;

$R^6$ is hydrogen, $C_{1-6}$ alkyl, $C_{1-4}$ alkoxy-$C_{1-4}$ alkyl, $C_{2-6}$ alkenyl, $C_{1-6}$ alkoxy, $C_{3-8}$ cycloalkyl, $C_{1-4}$ carbalkoxy, or CO₂H;

$R^7$ is hydrogen, $C_{1-4}$ alkoxy-$C_{1-4}$ alkyl, Y-substituted $C_{1-6}$ alkyl, Y-substituted $C_{3-6}$ alkenyl,

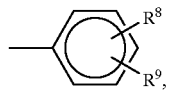

or —(CH₂)ₙ—Z;

$R^8$ is hydrogen, halogen, $C_{1-6}$ alkyl, alkoxy or nitro;

$R^9$ is hydrogen, halogen, $C_{1-6}$ alkyl, alkoxy, alkylcarbonyl, $C_{3-6}$ alkenyoxy, di $C_{1-4}$ alkylamino, di $C_{1-4}$ alkylamino-$C_{1-6}$ alkoxy, hydroxy, —O₂C—$C_{1-4}$ alkyl, phenoxy, or trifluoromethyl;

m and n are zero or 1;

Y is $C_{3-8}$ cycloalkyl, cyano, CO₂H, di $C_{1-4}$ alkylamino, hydroxy or

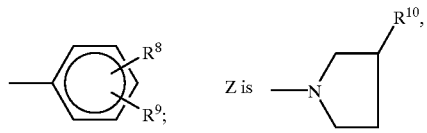

Z is 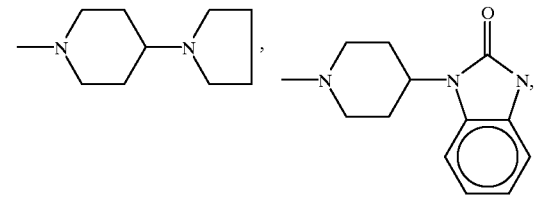

-continued

[chemical structures]

in which

R is hydrogen or $C_{1-4}$ alkyl;

$R^{10}$ is hydrogen, hydroxy, or $NCO_2R$;

$R^{11}$ is $C_{1-6}$ alkyl, $C_{3-8}$ cycloalkyl, —$CO_2R$, formyl, hydroxy-$C_{1-6}$ alkyl, pyridine or $R^{16}$-substituted phenyl;

$R^{12}$ is hydrogen, $C_{1-6}$ alkyl, or cyano;

$R^{13}$ is hydrogen or phenyl;

$R^{14}$ is hydrogen or

[chemical structure]

;

$R^{15}$ is hydrogen, halogen, or $C_{1-4}$ alkyl;

$R^{16}$ is $C_{1-4}$ alkoxy and nitro; or $Ar^1$ and $Ar^2$ are independently selected from the group consisting of

[chemical structure with $R^{17}$]

with $R^{17}$ being hydrogen, halogen, $C_{1-4}$ alkyl or alkoxy.

2. A compound of claim 1 wherein $Ar^1$ and $Ar^2$ are phenyl.

3. A compound of claim 1 wherein $R^4$ is halogen, $C_{1-6}$ alkyl, formyl, carboxamido, cyano, nitro, or trifluoromethyl.

4. A compound of claim 1 wherein $R^4$ is —$(CH_2)_m$—$NR^6R^7$.

5. A compound of claim 4 wherein $R^6$ is hydrogen.

6. A method of promoting weight loss or treating eating disorders in a mammal comprising administration to a mammalian host of an amount of a compound of Formula II or a pharmaceutically acceptable salt or hydrate thereof, effective in promoting weight loss and treating eating disorders (II)

[chemical structure of Formula II]

wherein A and B are independently selected from the group consisting of furanyl, thienyl, indole, or phenyl;

X is oxygen or sulfur;

$R^1$ is hydrogen or halogen;

$R^2$ is hydrogen, halogen, $C_{1-6}$ alkyl, alkoxy, cyano, or trifluoromethyl;

$R^3$ is hydrogen, halogen, cyano, or trifluoromethyl;

$R^4$ is hydrogen, halogen, $C_{1-6}$ alkyl, formyl, carboxamido, cyano, nitro, or —$(CH_2)_m$—$NR^6,R^7$;

$R^5$ is hydrogen, halogen, or $C_{1-6}$ alkoxy;

$R^6$ is hydrogen, $C_{1-6}$ alkyl, $C_{1-4}$ alkoxy-$C_{1-4}$ alkyl, $C_{2-6}$ alkenyl, $C_{1-6}$ alkoxy, $C_{3-8}$ cycloalkyl, $C_{1-4}$ carbalkoxy, or $CO_2H$;

$R^7$ is hydrogen, $C_{1-4}$ alkoxy-$C_{1-4}$ alkyl, Y-substituted $C_{1-6}$ alkyl, Y-substituted $C_{3-6}$ alkenyl,

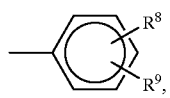

or —(CH$_2$)$_n$—Z;

$R^8$ is hydrogen, halogen, $C_{1-6}$ alkyl, alkoxy or nitro;

$R^9$ is hydrogen, halogen, $C_{1-6}$ alkyl, alkoxy, alkylcarbonyl, C alkenyoxy, di $C_{1-4}$ alkylamino, di $C_{1-4}$ alkylamino-$C_{1-6}$ alkoxy, hydroxy, —O$_2$C—C$_{1-4}$ alkyl, phenoxy, or trifluoromethyl;

m and n are zero or 1;

Y is $C_{3-8}$ cycloalkyl, cyano, CO$_2$H, di $C_{1-4}$ alkylamino, hydroxy or

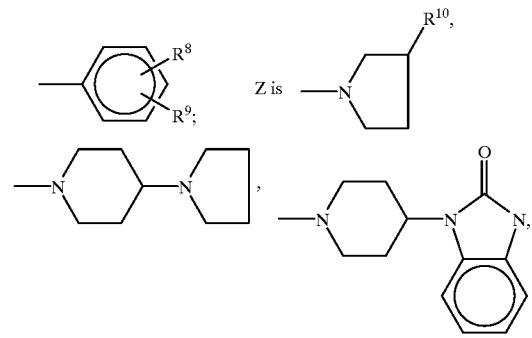

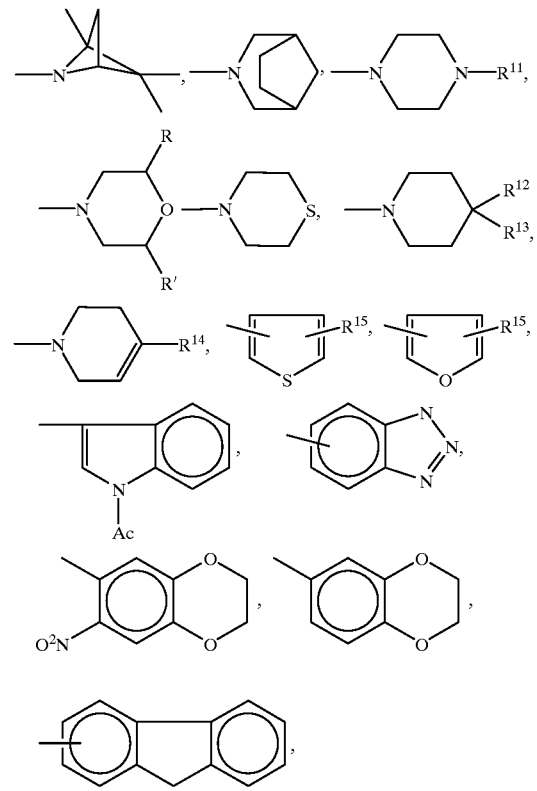

-continued

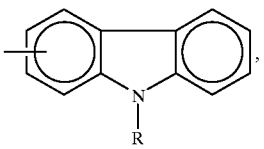

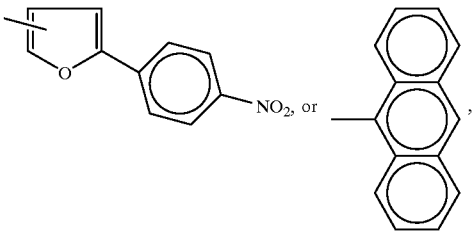

in which

R is hydrogen or $C_{1-4}$ alkyl;

$R^{10}$ is hydrogen, hydroxy, or NCO$_2$R;

$R^{11}$ is $C_{1-6}$ alkyl, $C_{3-8}$ cycloalkyl, —CO$_2$R, formyl, hydroxy-$C_{1-6}$ alkyl, pyridine or $R^{16}$-substituted phenyl;

$R^{12}$ is hydrogen, $C_{1-6}$ alkyl, or cyano;

$R^{13}$ is hydrogen or phenyl;

$R^{14}$ is hydrogen or

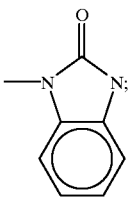

$R^{15}$ is hydrogen, halogen, or $C_{1-4}$ alkyl; and $R^{16}$ is $C_{1-4}$ alkoxy or nitro.

7. A method of promoting weight loss or treating eating disorders in a mammal comprising administration to a mammalian host of an amount of a Formula I compound as claimed in claim 1, effective in promoting weight loss and treating eating disorders.

8. A pharmaceutical composition for use in promoting weight loss or treating eating disorders, the composition comprising a weight loss promoting and eating disorder treating amount of a Formula I compound claimed in claim 1 in combination with a pharmaceutically acceptable carrier.

9. A pharmaceutical composition for use in promoting weight loss or treating eating disorders, the composition comprising a weight loss promoting and eating disorder treating amount of a Formula II compound claimed in claim 6 in combination with a pharmaceutically acceptable carrier.

* * * * *